United States Patent [19]

Dowbenko et al.

[11] 4,206,104
[45] Jun. 3, 1980

[54] N,N'-DIHYDROXYALKYL ESTER SUBSTITUTED IMIDAZOLIDINEDIONES AND COATING COMPOSITIONS CONTAINING SAME

[75] Inventors: Rostyslaw Dowbenko, Gibsonia; Ronald J. Lewarchik, Natrona Heights; William J. Birkmeyer, Oakmont, all of Pa.

[73] Assignee: PPG Industries, Inc., Pittsburgh, Pa.

[21] Appl. No.: 950,106

[22] Filed: Oct. 10, 1978

[51] Int. Cl.$^2$ .................. C08L 61/10; C08L 61/28
[52] U.S. Cl. .................. 260/29.3; 252/182;
260/29.2 TN; 260/29.4 R; 260/32.8 N;
260/31.4 R; 260/33.2 R; 260/33.6 R; 428/460;
525/417; 525/908; 528/45; 528/51; 528/73;
528/271; 528/367; 528/368; 548/312
[58] Field of Search .............. 528/368, 421, 423, 271,
528/87, 367, 45, 73; 252/182; 548/312;
260/29.3, 29.4 R, 29.2 TN, 32.8 N, 33.2 R, 33.6
R, 846, 849, 856, 858

[56] References Cited

U.S. PATENT DOCUMENTS

| | | | |
|---|---|---|---|
| 3,808,226 | 4/1974 | Habermeier et al. | 260/309.5 |
| 3,852,302 | 12/1974 | Habermeier et al. | 260/309.5 |
| 3,928,298 | 12/1975 | Wolf et al. | 548/312 |
| 4,028,378 | 6/1977 | MacFadyen | 548/312 |

Primary Examiner—Theodore E. Pertilla
Attorney, Agent, or Firm—Charles R. Wilson

[57] ABSTRACT

Resin mixtures of N,N'-dihydroxyalkyl ester substituted imidazolidinediones are especially useful in coating compositions having a low organic solvent content. The substituted imidazolidinediones have the formula

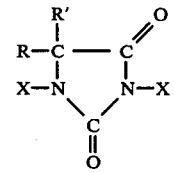

wherein R and R' are independently hydrogen or hydrocarbon groups having from 1 to 8 carbon atoms, X is

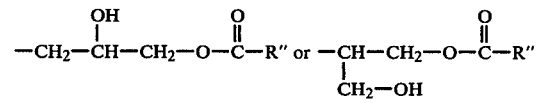

where the R" groups are independently hydrocarbon groups having from 1 to 17 carbon atoms.

33 Claims, No Drawings

N,N'-DIHYDROXYALKYL ESTER SUBSTITUTED IMIDAZOLIDINEDIONES AND COATING COMPOSITIONS CONTAINING SAME

BACKGROUND OF THE INVENTION

The subject invention relates to novel imidazolidinediones, their process of making and coating compositions containing them. More particularly, it relates to resin mixtures of N,N'-dihydroxyalkyl ester substituted imidazolidinediones and their use in coating compositions.

There have been recent concerns as to the polluting effects and health concerns associated with the use of organic solvents. Many useful coating compositions contain appreciable amounts of organic solvents. Precautions in the use of the coating compositions and the installation of solvent recovery systems have alleviated some of the concerns. However, it would still be desirable to formulate coating compositions containing little or no organic solvent.

Various attempts have been made to lower the organic solvent content in coating compositions. One line of work has concentrated on using water as the liquid carrier in place of the organic solvent. However, this has necessitated changes in the resin formulations with a consequent change in performance obtained from the coating compositions.

Another line of work has attempted to formulate coating compositions containing a high solids content, and thus low organic solvent content. The problem associated with many of the high solids coating compositions has been the fact such compositions normally are highly viscous and are hard to apply using conventional coating techniques. The formulation of coating compositions having a low organic solvent content which also possess a viscosity which allows the compositions to be applied by conventional techniques would be most desirable.

There have now been found novel compounds which when properly formulated into coating compositions provide compositions which can be readily applied and give coatings having a desired set of properties.

As used herein, all percents and ratios are by weight unless otherwise indicated.

SUMMARY OF THE INVENTION

The resin mixtures of N,N'-dihydroxyalkyl ester substituted imidazolidinediones of this invention have the formula:

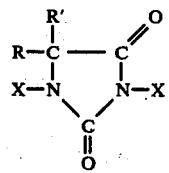

wherein R and R' are independently hydrogen or hydrocarbon groups having from 1 to 8 carbon atoms, X is

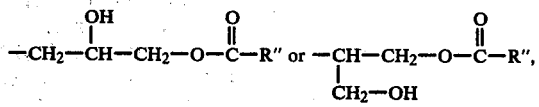

with the R" groups being independently hydrocarbon groups having from 1 to 17 carbon atoms. These imidazolidinediones are made by a one-step process of reacting a 2,4-imidazolidinedione with a glycidyl ester.

The above substituted imidazolidinediones are especially useful when formulated with a crosslinking agent selected from the group consisting of aminoplasts, isocyanates, blocked isocyanates, phenoplasts and mixtures thereof to form coating compositions. The coating compositions can have an organic solvent content of below about 40 percent.

DETAILED DESCRIPTION OF THE INVENTION

The following paragraphs describe the N,N'-dihydroxyalkyl ester substituted imidazolidinediones, their process of making and their use in coating compositions.

Resin mixtures of N,N'-dihydroxyalkyl ester substituted imidazolidinediones of this invention have the formula:

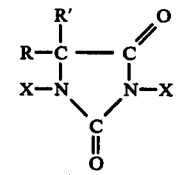

wherein R and R' are independently hydrogen or hydrocarbon groups having from 1 to 8 carbon atoms, X is

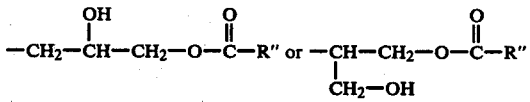

where the R" groups are independently hydrocarbon groups having from 1 to 17 carbon atoms.

The above-described N,N'-dihydroxyalkyl ester substituted imidazolidinediones are manufactured from the reaction product of a 2,4-imidazolidinedione and a glycidyl ester. Preferably a 1:2 molar ratio of the imidazolidinedione and glycidyl ester is used. The 2,4-imidazolidinediones have the formula:

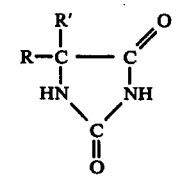

R and R' represent hydrogen groups, alkyl groups or, when joined, a cycloalkyl group. (It should be understood that the R and R' groups can be the same or different.) Preferably R and R' are alkyl groups having from 1 to 5 carbon atoms. The N-heterocyclic compound 2,4-imidazolidinedione is commonly referred to as hydantoin. Examples of substituted 2,4-imidazolidinediones which can be used are 5-methyl-2,4-imidazolidinedione, 5,5-dimethyl-2,4-imidazolidinedione, 5-methyl-5-ethyl-2,4-imidazolidinedione, 5-ethyl-5-amyl-2,4-imidazolidinedione, 5-propyl 2,4-imidazolidinedione, 5-isopropyl-2,4-imidazolidinedione and 5,5-pentamethylene-2,4-imidazolidinedione.

Glycidyl esters which are reacted with the 2,4-imidazolidinedione have the formula:

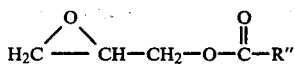

wherein R″ is a hydrocarbon group having from 1 to 17 carbon atoms. The hydrocarbon group can be saturated or unsaturated, aliphatic or cyclic in nature. Thus R″ can be an alkyl group having from 1 to 17 carbon atoms or an alkenyl group having from 2 to 17 carbon atoms or an aryl or alkylaryl group having from 6 to 10 carbon atoms. Examples of glycidyl esters are glycidyl acetate, glycidyl propionate, glycidyl methyl maleate, glycidyl stearate, glycidyl benzoate and glycidyl oleate. Preferred are the glycidyl esters where the R″ group is an alkyl group having from 7 to 17 carbon atoms. A particularly preferred glycidyl ester is a glycidyl ester of a saturated synthetic tertiary monocarboxylic acid having 9-11 carbon atoms.

The reaction of the imidazolidinedione and the glycidyl ester occurs over a wide range of temperatures, preferably from about 50° C. to about 200° C. A suitable catalyst such as a tertiary amine, quaternary phosphonium salt, quaternary ammonium salt, butyl stannoic acid or para-toluenesulfonic acid is used in the reaction. The reaction product is a mixture of N,N′-dihydroxyalkyl ester substituted imidazolidinediones with primary or secondary carbon atom attachment to the nitrogen atoms depending on how the epoxide groups open.

The N,N′-dihydroxyalkyl ester substituted imidazolidinediones are a mixture of compounds which have relatively low molecular weight, yet are substantally non-volatile upon exposure to elevated temperatures. The compounds can be thinned with a small amount of solvent to substantially reduce their viscosity. These properties make them especially useful in coating compositions where only a low level of organic solvent can be tolerated. Thus coating compositions can be formulated with the substituted imidazolidinediones and suitable crosslinking agents using little or no organic solvent. The resultant compositions have a low viscosity and can be applied using conventional coating techniques. Moreover, coatings resulting from the compositions are durable, have a good appearance and can have a high gloss.

Coating Compositions

Coating compositions of this invention consist essentially of from about 5 percent to about 90 percent, preferably from about 10 percent to about 50 percent of the above N,N′-dihydroxyalkyl ester substituted imidazolidinedione, and from about 5 percent to about 80 percent, preferably from about 20 percent to about 60 percent, of a suitable crosslinking agent. Examples of crosslinking agents are the aminoplasts, isocyanates, blocked isocyanates, phenoplasts and mixtures thereof. Preferred are the aminoplasts and blocked isocyanates. The aforedescribed classes of cross-linking agents are described in more detail in the following paragraphs.

Aminoplast resins are based on the addition products of formaldehyde, with an amino-or amido-group carrying substance, e.g., urea, ethylene diurea, ethylene urea, melamine and benzoguanamine. Condensation products obtained from the reaction of alcohols and formaldehyde with melamine, urea or benzoguanamine are preferred herein. Useful alcohols used to make etherified products are monohydric alcohols such as methanol, ethanol, propanol, butanol, benzyl alcohol and butoxyethanol. An etherified melamineformaldehyde resin is the preferred aminoplast resin. U.S. Pat. No. 4,075,141, Porter et al, Feb. 21, 1978 contains a description of useful aminoplast resins and is incorporated herein by reference.

Isocyanates useful as a crosslinking agent include any of the many organic isocyanates available. Examples include p-phenylene diisocyanate, biphenyl diisocyanate, toluene diisocyanate, 3,3′-dimethyl-4, 4′-biphenylene diisocyanate, 1,4-tetramethylene diisocyanate, hexamethylene diisocyanate, 2,2,4-tri-methylhexane-1,6-diisocyanate, methylene bis-(phenylisocyanate), isophorone diisocyanate, 1,2,4-benzene triisocyanate, polymethylene polyphenyl isocyanate, bis-(isocyanatocyclohexyl)methane and methyl cyclohexyl diisocyanate, as well as derivatives thereof.

Blocked isocyanates containing substantially no free isocyanate groups and relatively inactive at room temperature are very useful cross-linking agents. Typical blocking agents are the phenols, thiols, oximes, caprolactams, and secondary aromatic amines. Many of these compounds are commercially available. "The Chemistry of Organic Film Formers", Robert E. Kreiger Pub. Co., copyrighted 1977, by D. H. Solomon, pp. 216-217, contains a description of many blocked isocyanates that can be used here. The disclosure of this publication is herein incorporated by reference.

Phenoplast resins include the condensation products of an aldehyde with a phenol. Formaldehyde is a preferred aldehyde. Various phenols can be used, e.g., phenol per se, cresol, para-phenylphenol, para-tetriarybutylphenol, para-tertiaryamylphenol and cyclopentylphenol. The methylol phenol esters described in U.S. Pat. No. 2,597,330 (herein incorporated by reference) are especially useful.

The coating compositions consist essentially of the aforedescribed substituted imidazolidinediones and the crosslinking agents. Generally, however, coating composition additives are included in the compositions. A solvent such as water or an organic solvent, e.g., the ketones, ethylene glycol monoalkyl ether acetates, the mono- and dialkyl ethers of ethylene and propylene glycol, xylene, toluene and lower alcohols can be used. The level of the organic solvent in the composition, however, is less than about 40 percent, preferably less than about 30 percent, of the composition. Other coating composition additives include pigments, fillers, antioxidants, flow control agents, surfactants, catalysts and reactive diluents. Other curable resins can also be included in the coating compositions, provided such resins do not exceed about 60 percent of the composition.

The coating compositions are applied by any convenient method, include spraying, dipping and flow coating. The compositions have been found especially useful for the coating of metal substrates such as automotive parts.

The following examples are illustrative of the described invention, with Example I representing a preferred embodiment. Reaction products of the described processes are the N,N'-dihydroxyalkyl ester substituted imidazolidinediones of this invention.

EXAMPLE I

A three-liter reaction flask is set up with heating means, stirring means and a nitrogen sparge. The reaction vessel is charged with 320 grams of 5,5-dimethyl-2,4-imidazolidinedione, 1,220 grams of a glycidyl ester of Versatic 911 acid (available from Shell Chemical Co., as Cardura E) and 4.6 grams of butyl stannoic acid. The mixture is heated to 150° C. over a 6½ hour period. At the end of this time, the flask is sampled and found to contain the desired imidazolidinedione. The mixture has a viscosity of Z-7, an acid number of 0.5, hydroxyl number of 148 and contains substantially no volatiles.

EXAMPLE II

A reaction flask set up as in Example I is charged with 198 grams of 5-ethyl-5-amyl-2,4-imidazolidinedione, 488 grams of the Cardura E and 2.7 grams of ethyltriphenylphosphonium iodide. The mixture is heated to 120° C. and then allowed to exotherm to 190° C. The mixture is held at the elevated temperatures for about 7½ hours. At the end of this hold period, the reaction mixture has a viscosity of Z-5, a hydroxyl number of 133.8 and contains substantially no volatiles.

EXAMPLE III

A coating composition is formulated as follows:

|  | Percent |
| --- | --- |
| Resin mixture of Example I | 13.2 |
| Aminoplast resin[1] | 21.9 |
| Pigment paste[2] | 47.5 |
| Microgel dispersion[3] | 8.0 |
| Para-toluenesulfonic acid | 1.4 |
| Phenyl acid phosphate | 0.4 |
| Methyl ethyl ketone | 7.6 |

[1] The aminoplast resin is available from the Monsanto Co. as Resimine 755.
[2] The pigment paste contains 63 percent pigment; 11 percent grind resin of 16 percent hydroxyethyl acrylate, 2 percent acrylic acid, 27 percent styrene, 21 percent 2-ethylhexyl acrylate and 34 percent butyl methacrylate; and 26 percent Ester Diol 204 available from the Union Carbide Corp.
[3] The microgel dispersion corresponds to the dispersion described in Example II of commonly assigned copending application Serial No. 805,679, filed June 13, 1977.

The above composition is readily sprayed onto metal panels at a level sufficient to give a 2 mil dry film thickness. The coated panels, after baking at 120° C. for 30 minutes, have a satisfactory appearance as well as a durable finish as measured by their good solvent resistance, water resistance and acid resistance.

EXAMPLE IV

A coating composition is formulated in the same manner as Example III except the resin mixture of Example II is used in place of the resin mixture of Example I at the same level. Substantially the same satisfactory results are obtained when the composition is applied and tested as in Example III.

The above examples illustrate processes for making the resin mixtures of N,N'-dihydroxyalkyl ester substituted imidazolidinediones of this invention and their use in coating compositions.

What is claimed is:

1. A resin mixture of N,N'-dihydroxyalkyl ester substituted imidazolidinediones having the formula:

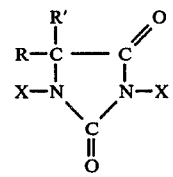

wherein R and R' are independently hydrogen or hydrocarbon groups having from 1 to 8 carbon atoms, X is

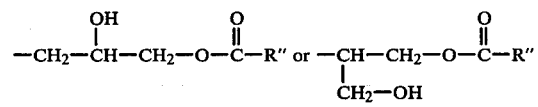

where the R" groups are independently hydrocarbon groups having from 1 to 17 carbon atoms.

2. The resin mixture of claim 1, wherein R and R' are hydrogens.

3. The resin mixture of claim 1, wherein R and R' are alkyl groups.

4. The resin mixture of claim 3, wherein the alkyl groups have from 1 to 5 carbon atoms.

5. The resin mixture of claim 4, wherein the alkyl groups are joined to form a cycloalkyl group.

6. The resin mixture of claim 1, wherein R is hydrogen and R' is an alkyl group.

7. The resin mixture of claims 2, 3 or 6, wherein the R" groups are alkyl groups.

8. The resin mixture of claim 7, wherein the R" alkyl groups have from 7 to 17 carbon atoms.

9. The resin mixture of claim 8, wherein the R" alkyl groups are tertiary alkyl groups.

10. The resin mixture of claims 2, 3 or 6, wherein the R" groups are alkenyl groups.

11. The resin mixture of claims 2, 3 or 6, wherein the R" groups are aryl or alkylaryl groups having from 6 to 10 carbon atoms.

12. A process for making a resin mixture of N,N'-dihydroxyalkyl ester substituted imidazolidinediones comprising the step of reacting (1) an imidazolidinedione of the formula:

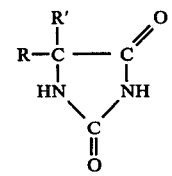

wherein R and R' are independently hydrogen or hydrocarbon groups having from 1 to 8 carbon atoms; with (2) a glycidyl ester of the formula:

wherein R" is a hydrocarbon group having from 1 to 17 carbon atoms at a temperature of from about 50° C. to about 200° C. in the presence of a catalyst so as to obtain a mixture of compounds having the formula:

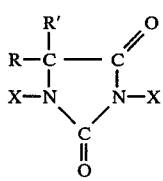

where X is

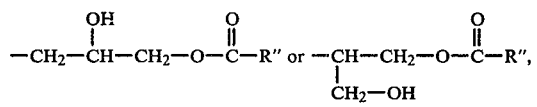

with R, R' and R'' being as defined above.

13. The process of claim 12, wherein R and R' are hydrogens.

14. The process of claim 12, wherein R and R' are alkyl groups.

15. The process of claim 14, wherein the R and R' groups have from 1 to 5 carbon atoms.

16. The process of claim 15, wherein the R and R' alkyl groups are joined to form a cycloalkyl group.

17. The process of claim 12, wherein R is hydrogen and R' is an alkyl group.

18. The process of claims 13, 14, or 17, wherein the R'' groups are alkyl groups have from 7 to 17 carbon atoms.

19. A coating composition containing less than about 40 percent organic solvent, consisting essentially of:
(a) from about 5 percent to about 90 percent of a resin mixture of N,N'-dihydroxyalkyl ester substituted imidazolidinediones having the formula:

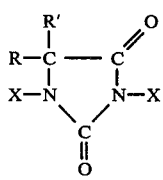

wherein R and R' are independently hydrogen or hydrocarbon groups having from 1 to 8 carbon atoms, X is

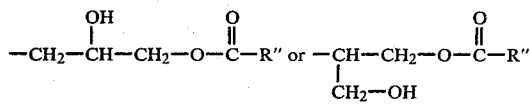

where the R'' groups are independently hydrocarbon groups having from 1 to 17 carbon atoms; and
(b) from about 5 percent to about 80 percent of a crosslinking agent selected from the group consisting of aminoplasts, isocyanates, blocked isocyanates, phenoplasts and mixtures thereof.

20. The composition of claim 19, wherein the composition contains less than about 30 percent organic solvent.

21. The composition of claim 19, wherein R and R' are hydrogens.

22. The composition of claim 19, wherein R and R' are alkyl groups.

23. The composition of claim 22, wherein the alkyl groups have from 1 to 5 carbon atoms.

24. The composition of claim 23, wherein the alkyl groups are joined to form a cycloalkyl group.

25. The composition of claim 19, wherein R is hydrogen and R' is an alkyl group.

26. The composition of claims 21, 22, or 25, wherein the R'' groups are alkyl groups.

27. The composition of claim 26, wherein the R'' alkyl groups have from 7 to 17 carbon atoms.

28. The composition of claims 21, 22 or 25, wherein the R'' groups are alkenyl groups.

29. The composition of claims 21, 22, or 25, wherein the R'' groups are aryl or alkylaryl groups having from 6 to 10 carbon atoms.

30. The composition of claim 19, wherein the crosslinking agent is an aminoplast.

31. The composition of claim 19, wherein the crosslinking agent is a blocked isocyanate.

32. The composition of claims 19, 30 or 31, wherein the substituted imidazolidinediones represent from about 10 percent to 50 percent of the composition and the crosslinking agent from about 20 percent to about 60 percent of the composition.

33. The process of claim 12 wherein the catalyst is a tertiary amine, quaternary phosphonium salt, quaternary ammonium salt, butyl stannoic acid or para-toluenesulfonic acid.

* * * * *